United States Patent [19]

Williams et al.

[11] 4,029,675

[45] June 14, 1977

[54] PROCESS FOR PREPARATION OF LACTONE-ESTERS

[75] Inventors: Albert L. Williams; El-Ahmadi I. Heiba, both of Princeton, N.J.

[73] Assignee: Mobil Oil Corporation, New York, N.Y.

[22] Filed: Aug. 13, 1975

[21] Appl. No.: 604,298

[52] U.S. Cl. .......................... 260/343.6; 252/56 R; 260/537 R; 260/485 L

[51] Int. Cl.$^2$ ....................................... C07D 307/32

[58] Field of Search ................................. 260/343.6

[56] References Cited

UNITED STATES PATENTS 3,155,685  11/1964  Prill et al. ........................ 260/343.5

Primary Examiner—Cecilia M. S. Jaisle
Attorney, Agent, or Firm—Charles A. Huggett; Raymond W. Barclay; Howard M. Flournoy

[57] ABSTRACT

A process for the continuous preparation of lactone-esters which comprises: passing a liquid feed of a branched-chain alkenylsuccinic anhydride containing a chain wherein branching is derived from $C_3$ to $C_{10}$ olefins, and an alcohol in a hydrocarbon solvent through a packed bed of a cationic exchange resin catalyst containing acid groups, in a reaction zone, said reaction zone being maintained at a pressure from about 1 to about 20 atmospheres and at a temperature from about 120° C to about 160° C.

4 Claims, No Drawings

PROCESS FOR PREPARATION OF LACTONE-ESTERS

BACKGROUND OF THE INVENTION

1. Field of the Invention

This invention relates to lactone-esters and relates more particularly to an improved process for manufacturing lactone-esters and their use, particularly in lubricating and other organic media where good detergency properties are a requisite.

2. Description of the Prior Art.

Lactone-esters have found wide utility as dispersants in lubricating compositions, such as oils (including hydraulic oils, transmission fluids, gear oils and the like) and greases. They are also useful as intermediates for the synthesis of such products as lactone-acids and lactone-amides, useful in the manufacture of soaps and dispersants. Prior to the present invention, they have been prepared from half-esters of alkenylsuccinic anhydrides in a batch process, as described, for example, in U.S. Pat. No. 3,155,685. Lactone-esters have also been prepared directly from alcohols and alkenyl-anhydrides in a batch process employing an activated alkenyl group. The use of a batch process, however, presents certain disadvantages, as more fully hereinafter described.

SUMMARY OF THE INVENTION

In accordance with the present invention, a process is provided for the continuous preparation of lactone-esters, which comprises passing a liquid feed of a branched-chain alkenylsuccinic anhydride containing a chain wherein branching is derived from $C_3$ to $C_{10}$ olefins, and an alcohol in a hydrocarbon solvent through a packed bed of a cationic exchange resin catalyst containing acid groups, in a reaction zone, said reaction zone being maintained at a pressure from about 1 to about 20 atmospheres and at a temperature from about 120° C to about 160° C, and removing water as an azeotrope.

By the use of water-azeotroping solvent and increased pressure, the novel process can be operated at a relatively higher temperature than that of a batch process with consequent increased rate of output of lactone-ester product. This product is of relatively higher purity than that obtained in a comparable reaction time in a batch process. Furthermore, by operating with a solvent to assist in water removal, the catalyst life is increased manyfold over that obtained in a batch process, and attrition of catalyst beads is greatly reduced in the absence of stirring. In addition, the continuous process conditions facilitate the formation of lactone-esters and permit good yields from branched-chain alkenylsuccinic anhydrides, as, for example, from polypropenylsuccinic anhydrides. However, it is also found that normal alkenylsuccinic anhydrides with no activation of the double bond give relatively lower yields of lactone-ester but produce a large amount of diester instead. In such instances, diesters having double bonds activated by chain branching can be converted to lactone esters through the loss of a molecule of alcohol in the continuous process. Likewise, acid-esters (half-esters) can also can be converted to lactone-esters, in the above-described continuous process.

The branched-chain alkenylsuccinic anhydride employed in the above-described novel continuous process of the present invention contains a chain wherein branching is derived from $C_3$ to $C_{10}$ olefins and, for most applications, contains from about 8 to about 300 carbon atoms. Representative examples of the branched-chain alkenylsuccinic anhydride are: polypropenylsuccinic anhydride, polyisobutenylsuccinic anhydride, poly-1-butenylsuccinic anhydride, and poly-1-decenylsuccinic anhydride.

The alcohol of the liquid feed is preferably an aliphatic alcohol. Representative examples of the alcohol are methyl alcohol, hexyl alcohol, trimethylolpropane, octanethiol, ethyl alcohol, n-butyl alcohol, isopropyl alcohol, and cyclohexanol.

Any hydrocarbon solvent in which the branched-chain alkenylsuccinic anhydride and alcohol are soluble may be employed. Representative examples of this solvent are; n-octane, n-heptane, methylcyclohexane, benzene, toluene, mixed xylenes, petroleum naphtha, ethylbenzene, light petroleum oils, and mixtures of these solvents.

The catalyst employed in the reaction, as hereinbefore described, is a cationic exchange resin catalyst containing acid groups. These are macroticular acid ion exchange resins typified by the presence of sulfonic acid groups, e.g. sulfonated styrene-divinylbenzene copolymer exchange resins such as those commercially available as Amberlyst 15.

The above-described process in which the branched-chain alkenylsuccinic anhydride and alcohol, in a hydrocarbon solvent, is passed through the catalyst bed, is conducted at a temperature from about 120° C. to about 160° C. For most applications, the lactone-ester, is satisfactorily employed as a detergent or dispersant in organic media in an amount from about 0.001 to about 10%, by weight, and preferably in an amount from about 0.5 to about 5% by weight, of the total weight of the lubricant.

The lactone-esters, produced by the above-described continuous process may be incorporated in any lubricating media which may comprise liquid hydrocarbon oils in the form of a grease in which any of the aforementioned oils are employed as a vehicle. In general, mineral oils employed as the lubricant, or grease vehicle, may be of any suitable lubricating viscosity range, as for example, from about 45 SSU at 100° F to about 6,000 SSU at 100° F, and, preferably from about 50 to about 250 SSU at 210° F.

These oils may have viscosity indexes varying from below zero to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils, or synthetic oils employed as the vehicle for the grease, are desired in preference to mineral oils or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, flourocarbons, silicate esters, silanes, esters of phosphorous-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis-(p-phenoxy phenyl) ether, phenoxy phenylether, etc.

DESCRIPTION OF SPECIFIC EMBODIMENTS

The following examples will serve to illustrate the novel continuous process of the present invention for producing lactone-esters, the latter being particularly useful as detergents in organic media.

EXAMPLE 1

A stainless steel column 14.5 cm. in length and 1.4 cm. in inside diameter was packed with 11.5 g. (19 ml.) of the above-described sulfonated styrene-divinylbenzene copolymer exchange resin commercially available as Amberlyst 15. Temperature of the bed was measured by a thermocouple in the reaction tube, and heat was supplied by heating tapes around the stainless steel reactor. The inlet line to the bottom of the reaction was also heated to bring the feed stock to reactor temperature. The feed stock was prepared by dissolving 415.3 g. (0.208 mole) of alkenylsuccinic anhydride (a product having 25% of polybutene of formula weight 1400 mixed with 75% of the alkenyl anhydride, where the alkenyl group is of 1400 formula weight) in 420 ml. of n-octane plus 20 g. (0.624 moles) of methanol. This feed stock was pumped through the catalyst bed at 138° to 140° C at 0.5 hourly space velocity, with a pressure of 20 p.s.i.g. of nitrogen on the receiver. The n-octane and excess methanol were stripped under vacuum. Except for the feed stock remaining in the lines and column when the unit was shut down, the yield (410 g.) of the product (largely lactone-ester) was quantitative. Infrared anaylsis showed the composition of the product to be:

(gamma)-lactone-ester = 88%
Diester = 4%
Acid-ester = 8%

EXAMPLE 2

The reactor of Example 1 was charged with 11.5 g. of fresh catalyst as used in Example 1, and arranged as in Example 1. A feed stock was prepared by mixing 100 g. of xylene with 100 g. of an oil of mid-continent type having a viscosity of 43 S.U.S. at 210° F, and dissolving in this mixture 9.6 g. (0.30 mole) of methyl alcohol and 100 g. (0.050 mole) of alkenylsuccinic anhydride (a product having 25% of polybutene of formula weight 1400 mixed with 75% of the alkenyl anhydride, where the alkenyl group is of 1400 formula weight). This feed stock was pumped through the catalyst bed at 137° to 140° C at 0.5 hourly space velocity, with a pressure of 20 p.s.i.g. of nitrogen on the receiver. Xylene and excess methyl alcohol were stripped from the product in oil by vacuum evaporation. The yield (186 g.) was quantitative except for feed stocks remaining in the lines and column. Infrared analysis of the product at the 50% level in process oil showed:

(gamma)-lactone-ester = 79%
Diester = 9%
Acid-ester = 12%

EXAMPLE 3

A stainless steel column 59 cm. in length and 5.2 cm. in inside diameter, having a volume of 1250 cubic centimeters, was packed with 767 g. of fresh catalyst as used in Example 1. Heat was supplied to the reactor and to the feed inlet line by banks of electrical heating tapes. A thermocouple measured temperatures in the reactor tube. The catalyst bed was conditioned by pumping through 18 liters of n-octane at a 0.5 hourly space velocity while holding the reactor bed in a temperature range of 130°–140° C. The feed stock was prepared by dissolving 38.819 kg (20.32 moles) of alkenylsuccinic anhydride (a product having 21.6% of polybutene of formula weight 1400 mixed with 78.4% of the alkenylanhydride where the alkenyl group is of 1400 formula weight) in 54 liters of n-octane plus 1.953 kg (60.96 moles) of methanol. This feed stock was pumped through the catalyst bed at an inlet temperature in the range of 130°–138° C and an outlet temperature in the range of 134°–140° C. The hourly space velocity was 0.50, with a pressure of 20 p.s.i.g. of nitrogen on the receiver. The octane and excess methanol were distilled off under vacuum. The yield of product (39.09 kg) was quantitative except for feed stock remaining in the lines and column. Infrared analysis showed the composition of the product to be:

(gamma)-lactone-ester = 82%
Diester = 7%
Acid-ester = 11%

As hereinbefore described, the alkenylsuccinic anhydrides employed in the novel continuous process of the present invention are branched-chain and derived from $C_3$ to $C_{10}$ olefins. The criticality of employing branched-chain instead of straight-chain alkenylsuccinic anhydrides is apparent from the fact that failures were obtained from two different anhydrides prepared from straight-chain olefins.

EXAMPLE 4

The reactor of Example 1 was charged with 11.5 g. of fresh catalyst as used in Example 1, and arranged as in Example 1. A feed stock was prepared by dissolving 105 g. (0.36 mole) of n-tetradecenylsuccinic anhydride (from Humphrey Chemical Company) in 200 ml. of n-octane plus 34.6 g. (1.08 moles) of methanol. This feed stock was pumped through the catalyst bed at 132° C to 135° C at 0.5 hourly space velocity with a pressure of 20 p.s.i.g. of nitrogen on the receiver. The n-octane and methanol were stripped off under vacuum. The product of the reaction was shown by infrared spectra to be almost entirely diester. The content of lactone-ester in the product was less than 10%.

EXAMPLE 5

The reactor of Example 1 was charged with 11.5 g. of fresh catalyst as used in Example 1, and arranged as in Example 1. A feed stock was prepared by dissolving 101 g. (0.38 mole) of n-dodecenylsuccinic anhydride (from Humphrey Chemical Company) in 200 ml. of toluene plus 36.5 g. (1.14 moles) of methanol. This feed stock was pumped through the catalyst bed at 128° C to 134° C at 0.5 hourly space velocity with a pressure of 20 p.s.i.g. of nitrogen on the receiver. The toluene and methanol were stripped off under vacuum. The product of the reaction was shown by infrared spectra to be almost entirely diester. The content of lactone-ester in the product was less than 10%.

While this invention has been described with reference to preferred compositions and components therefor, it will be understood, by those skilled in the art, that the departure from preferred embodiments can be effectively made and are within the scope of the specification.

We claim:

1. A process for the continuous preparation of lactose-esters which comprises: passing a liquid feed of a $C_8$-$C_{300}$ branched-chain alkenylsuccinic anhydride containing a chain, wherein branching is derived from $C_3$ to $C_{10}$ olefins, and an alcohol or thiol selected from the group consisting of methyl alcohol, hexyl alcohol, trimethylolpropane, octanethiol, ethyl alcohol, n-butyl alcohol, isopropyl alcohol and cyclohexanol in a hydrocarbon solvent through a packed bed of a sulfonated styrene-divinylbenzene copolymer exchange resin catalyst, in a reaction zone, said reaction zone being maintained at a pressure from about 1 to about 20 atmospheres and at a temperature from about 120° C to about 160° C.

2. The process defined by claim 1 wherein the hydrocarbon solvent is selected from the group consisting of n-octane, n-heptane, methylcyclohexane, benzene, toluene, mixed xylenes, petroleum naphtha, ethylbenzene light petroleum oils and mixtures thereof.

3. The process of claim 1 wherein said branched-chain alkenylsuccinic anhydride is selected from the group consisting of polypropenylsuccinic anhydride, polyisobutenylsuccinic anhydride, poly-1-butenylsuccinic anhydride, and poly-1-decenylsuccinic anhydride.

4. The process defined by claim 1 wherein the lactone-ester product contains diesters and acid-esters as additional components, said diester or acid-ester are separated from said product and are passed through a packed bed of said catalyst to produce additional amounts of lactone-ester.

* * * * *

UNITED STATES PATENT AND TRADEMARK OFFICE
CERTIFICATE OF CORRECTION

PATENT NO. : 4,029,675
DATED : June 14, 1977
INVENTOR(S) : ALBERT L. WILLIAMS and EL-AHMADI I. HEIBA It is certified that error appears in the above-identified patent and that said Letters Patent are hereby corrected as shown below:

Column 5, Claim 1, line 2     "tose-esters" should read --tone-esters--.

*Signed and Sealed this*

*Twentieth* Day of *September 1977*

[SEAL]

Attest:

RUTH C. MASON
*Attesting Officer*

LUTRELLE F. PARKER
*Acting Commissioner of Patents and Trademarks*